United States Patent
Zyhowski et al.

(10) Patent No.: US 8,133,407 B2
(45) Date of Patent: Mar. 13, 2012

(54) SESQUITERPENE STABILIZED COMPOSITIONS

(75) Inventors: Gary Zyhowski, Lancaster, NY (US); Rajiv Ratna Singh, Getzville, NY (US); Raymond H. Thomas, Pendleton, NY (US); Mark W. Spatz, East Amherst, NY (US); Roy P. Robinson, Cheektowaga, NY (US); George J. Samuels, Williamsville, NY (US); Gregory J. Shafer, Chaffee, NY (US); Michael Van Der Puy, Amherst, NY (US); David P. Wilson, East Amherst, NY (US); John L. Welch, Buffalo, NY (US); Ronald P. Vogl, Springville, NY (US); Samuel F. Yana Motta, East Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 146 days.

(21) Appl. No.: 12/467,061

(22) Filed: May 15, 2009

(65) Prior Publication Data

US 2009/0283712 A1    Nov. 19, 2009

Related U.S. Application Data

(60) Provisional application No. 61/053,663, filed on May 15, 2008.

(51) Int. Cl.
*C09K 5/00* (2006.01)
*C11D 3/24* (2006.01)

(52) U.S. Cl. .............. 252/67; 252/68; 252/69; 510/408; 510/412; 510/463; 165/58; 165/63; 570/123; 570/126; 570/128; 570/134; 570/135; 570/136

(58) Field of Classification Search .................. 510/408, 510/412, 463; 252/67, 68, 69; 165/58, 63; 570/123, 126, 128, 134, 135, 136
See application file for complete search history.

(56) References Cited

U.S. PATENT DOCUMENTS

| | | | |
|---|---|---|---|
| 2006/0019857 A1* | 1/2006 | Wilson et al. | 510/408 |
| 2006/0043330 A1* | 3/2006 | Wilson et al. | 252/67 |
| 2008/0157022 A1* | 7/2008 | Singh et al. | 252/68 |
| 2011/0037017 A1* | 2/2011 | Leck | 252/68 |

* cited by examiner

*Primary Examiner* — Charles Boyer
(74) *Attorney, Agent, or Firm* — Colleen D. Szuch

(57) ABSTRACT

Provided is a composition comprising (a) at least one halogenated compound selected from the group consisting of $C_3$-$C_5$ hydrofluoroolefin, $CF_3I$, and combinations thereof, and (b) an effective stabilizing amount of a sesquiterpene selected from the group consisting of farnesol, farnesene, and mixtures thereof.

5 Claims, No Drawings

SESQUITERPENE STABILIZED COMPOSITIONS

CROSS-REFERENCE TO RELATED APPLICATIONS

This application claims priority benefit of U.S. Provisional Application No. 61/053,663, filed on May 15, 2008, which is incorporated herein by reference.

BACKGROUND

1. Field of Invention

This invention relates to a composition comprising at least one halogenated organic compound and a stabilizer. More particularly, the invention relates to a composition comprising a hydrofluoroolefin and a stabilizer.

2. Description of Related Art

Fluoroolefins and certain other compounds, such as $CF_3I$, have been proposed as replacements of chlorofluorocarbons, hydrochlorofluorocarbons, and hydrofluorocarbons which, conventionally, have been used as working fluids, refrigerants, solvents, blowing agents, and the like. Fluoroolefins and $CF_3I$ are characterized as having a low global warming potential (GWP) and little or no ozone depletion effect and, thus, are more environmentally friendly compared to chlorofluorocarbons, hydrochlorofluorocarbons, and hydrofluorocarbons. Moreover, fluoroolefins and $CF_3I$ have excellent refrigeration performance and generally are nontoxic and nonflammable.

The refrigerant's low global warming is due, in part, to the fact that these compounds are less chemically and thermally stable than their predecessor refrigerants. More particularly, fluids that have low GWP values typically have a reactive site, such an alkene's double bond, that advantageously increases the rate of decomposition in the atmosphere thus producing a short atmospheric lifetime. This reactive site in the molecule is usually not reactive enough to cause the substance to be so unstable that it's utility as a refrigerant or solvent in degraded. While these properties are typically maintained at low temperatures, the stability of low GWP refrigerants and solvents is jeopardized when they contact with conventional materials of construction of refrigeration systems at high temperatures (e.g., $\geq 50°$ C.).

It is also possible that the reactive sites of the low GWP materials can be the source of reaction during use and also during storage. Reactions such as polymerization or decomposition have been seen when some of these low GWP substances have been stored under extreme conditions. Even though many of these low GWP materials are fairly stable during use, they are measurably less stable than the long lived hydrofluorocarbons they replace.

In substituting low GWP substances which have this necessary reactive site in the molecule, there is a need to stabilize the fluid during storage and use if the fluid is subjected to extreme temperatures or long storage times. While conventional stabilizers for low GWP working fluids are often soluble in conventional lubricating oil, they are not soluble in the refrigerant itself. A stabilizer that is soluble in the refrigerant, and more preferably soluble in both the refrigerant and lubricant, would be advantageous.

SUMMARY OF THE INVENTION

Applicants have discovered that the addition of a sesquiterpene, preferably farnesol and/or farnesene, to a composition comprising one or more low GWP compounds, particularly trifluoroiodomethane ($CF_3I$), $C_3$-$C_5$ fluoroolefins, and combinations thereof, increases the chemical stability of the composition at high temperatures. More particularly, farnesol acts as radical scavenger in a composition comprising a combination of a stabilizer comprising farnesol and/or farnsene and a low GWP compound. For example, farnesol can slows the polymerization of HFO-1234yf and can slow the decomposition of $CF_3I$ to form R-23. Farnesol also slows the polymerization of polyalkylene glycol compressor lubricant. Moreover, farnesol and farnesene can be added directly to the refrigerant of a refrigeration system which facilitates its uniform distribution since the refrigerant has a low viscosity compared to conventional refrigeration system lubricants.

Accordingly, an aspect of the invention is a composition comprising (a) at least one halogenated compound selected from the group consisting of $C_3$-$C_5$ hydrofluoroolefin, $CF_3I$, and combinations thereof; and (b) an effective stabilizing amount of a sesquiterpene selected from the group consisting of farnesol, farnesene, and mixtures thereof. Preferred $C_3$-$C_5$ hydrofluoroolefins include tetrafluoropropenes, particularly 2,3,3,3-tetrafluoro-1-propene (HFO-1234yf) and 1,3,3,3-tetrafluoro-1-propene (HFO-1234ze).

According to another aspect of the invention, provided is a method for chemically stabilizing a refrigerant composition comprising mixing a refrigerant selected from the group consisting of HFO-1234yf, HFO-1234ze, $CF_3I$, and combinations thereof, with an effective stabilizing amount of a sesquiterpene selected from the group consisting of farnesol, farnesene, and mixtures thereof.

According to yet another aspect of the invention, provide is a method for stabilizing a solvent comprising (a) mixing a solvent comprising at least one halogenated compound selected from the group consisting of $C_3$-$C_5$ hydrofluoroolefin, $CF_3I$, and combinations thereof, with an effective stabilizing amount of a sesquiterpene selected from the group consisting of farnesol, farnsene, and mixtures thereof; and (b) increasing the temperature of the solvent to at least 50° C.

DETAILED DESCRIPTION OF PREFERRED EMBODIMENTS OF THE INVENTION

The present invention provides a composition comprising at least one low GWP, and an effective amount of a sesquiterpene stabilizer, preferably farnesol and/or farnsene. These compositions are particularly useful as solvents and/or refrigerants at high temperatures, but can also be used as blowing agents, aerosol propellants, fire extinguishants, and sterilants. As a refrigerant, the composition can be used as a heat transfer medium in refrigeration systems, refrigerators, air conditioning systems, heat pumps, chillers, and the like.

As used herein, the term "low GWP" refers to fluids that have a GWP of less than 500 relative to carbon dioxide. Preferably, they are fluids that have GWP values of less than 400. More preferably they have a GWP of 200 or less.

As used herein, the term "stabilizer" refers to inhibitor, stabilizers, scavengers. Such stabilizers mitigate chemical and/or thermal degradation of the stabilized compound and/or polymerization of the stabilized compound, particularly at temperatures at or above 50° C. and/or when the compound is stored for at least about 3 month, more preferably at least about 6 months, and even more preferably at least about 1 year.

As used herein, the term "effective amount" refers to an amount of stabilizer of the present invention which, when added to a composition comprising at least one fluoroolefin, results in a composition that will not degrade to produce as great a reduction in refrigeration performance when in use in a cooling apparatus as compared to the composition without stabilizer under similar storage and/or temperature conditions. Such effective amounts of stabilizer may be determined by way of testing under the conditions of standard test ASHRAE 97-2004. In a certain embodiment of the present invention, an effective amount may be said to be that amount of stabilizer that when combined with a composition comprising at least one fluoroolefin allows a cooling apparatus utilizing said composition comprising at least one fluoroolefin to perform at the same level of refrigeration performance and cooling capacity as if a composition comprising 1,1,1,2-tetrafluoroethane (R-134a), or other standard refrigerant (R-12, R-22, R-502, R-507A, R-508, R401A, R401B, R402A, R402B, R408, R-410A, R-404A, R407C, R-413A, R-417A, R-422A, R-422B, R-422C, R-422D, R-423, R-114, R-11, R-113, R-123, R-124, R236fa, or R-245fa) depending upon what refrigerant may have been used in a similar system in the past, were being utilized as the working fluid.

The term, "high temperature" with respect to operational and/or storage conditions of a low-GWP compound, means at least 50° C.

The term "farnesol" is the compound 3,7,11-trimethyl-2,6,10-dodecatrien-1-ol, including any and all stereoisomers thereof. Farnesol is a natural organic compound which is a sesquiterpene alcohol found as a colorless liquid and is insoluble in water, but miscible with oils. It has the chemical structure:

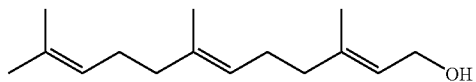

The term "farnesene" includes α-farnesene (i.e., 3,7,11-trimethyldocecadodeca-1,3,6,19-tetraene) and β-farnesene (i.e., 7,11-dimethyl-3-methylene-1,6,10-dodecatriene), including any and all stereoisomers thereof.

Preferred low-GWP compound include $C_3$-$C_5$ hydrofluoroolefin, $CF_3I$, and combinations thereof. Particularly preferred hydrofluoroolefins include HFO-1234yf, HFO-1234ze, and HFO-1233zd. Preferred low-GWP compounds include HFO-1234yf and combinations of HFO-1234yf and $CF_3I$.

HFO-1234yf, HFO-1234ze, HFO-1233zd, and $CF_3I$ are commercially available compounds and also can be synthesized by known methods.

Certain embodiments include effective amounts of stabilizer for use in the present invention that comprise from about 0.001 weight percent to about 10 weight percent, more preferably from about 0.01 weight percent to about 5 weight percent, even more preferably from about 0.3 weight percent to about 4 weight percent and even more preferably from about 0.3 weight percent to about 1 weight percent based on the total weight of compositions comprising at least one fluoroolefin as described herein. When a mixture of stabilizers or stabilizer blend is used, the total amount of the mixture or stabilizer blend may be present in the concentrations as described herein above.

Stabilizers can be introduced into the HFO-1234yf, HFO-1234ze, and/or $CF_3I$ refrigerant by various means at different points during manufacture of the refrigerant or later once the refrigerant has been charged to an air-conditioning system. Stabilizer can be added by in-line injection using metering valves and mass flow meters to meter in a pre-determined amount of stabilizer. In such fashion, stabilizer could be added during product blending or product packaging. Alternatively, stabilizer can be pumped into a blending tank containing the refrigerant. Load cells would facilitate addition of stabilizer to the proper amount by weight difference. Stabilizer may also be added to refrigerant by using density versus temperature data to convert the desired weight of stabilizer to a volume. The required volume of stabilizer could then be pumped or fed by gravity to the refrigerant blend tank.

Farnesol is soluble, for example, at up to 10% in 70% 1234yf/30% $CF_3I$. In cases where solubility of the stabilizer in one or both of the refrigerant components is inadequate, a small amount of another component such as compressor lubricant in which the stabilizer is soluble, can be added to increase the solubility of the stabilizer in the resulting matrix.

Composition comprising one or more low-GWP compounds and a stabilizing amount of farnesol and/or farnesene are characterized by a significant improvement in chemical stability at a temperature of about 50° C. and higher, particularly about 100° C. and higher, and more particularly about 200° C. and higher, compared to the low-GWP compounds without farnesol. Under these conditions, the low-GWP compounds demonstrated a significant reduction in thermal or chemical degradation, particularly polymerization and particularly with respect to reactions occurring at an olefinic double bond.

Once the stabilized refrigerant is charged to a system, prolonged system operation may result in decline of the effectiveness or availability of stabilizer. A system leak or system servicing may result in loss of lubricant. This too, diminishes the amount of stabilizer available in the system. The stabilizer shortfall can be made up by adding concentrated stabilizer in refrigerant if the refrigerant has leaked out. Small cans of stabilizer concentrate in refrigerant equipped with appropriate fittings, valves, and hose can be used to transfer stabilized refrigerant into the system. Likewise, the shortfall can be made up by adding concentrated stabilizer in oil if oil has leaked out. In-line stabilized oil capsules with compatible fittings for connection to standard service gauge sets can be used. If refrigerant and oil have both leaked out, the contents of such stabilized oil capsules can be pushed into the system using refrigerant. Manual oil injector pumps can be used to introduce make-up stabilized oil.

When it is determined that additional stabilizer needs to be added to a charged system and the full complement of refrigerant and oil are present in the system, a refrigerant recovery/recycle unit equipped with a stabilizer concentrate reservoir can be used to add stabilizer to the refrigerant. The refrigerant would be recovered using a vapor-recovery mode recovery unit. Any entrained oil would be stripped out in an oil separator. Refrigerant would be compressed, condensed, and filtered. Liquid refrigerant would then pass through an in-line vessel containing stabilizer. The stabilizer would be dissolved by the circulating refrigerant. As necessary, re-circulation of the refrigerant through the stabilizer-containing vessel could be conducted until the necessary amount of stabilizer is dissolved in the refrigerant. Using a sensing means such as refractive index, the circulation/re-circulation would be controlled. Once the proper amount of stabilizer was in solution, the recovery/recycle unit would dispense the stabilized refrigerant back into the A/C system. Other means to introduce stabilizer concentrate into recovered refrigerant within a recovery/recycle unit would include metering from a concentrate reservoir into a stream of circulating refrigerant or metering into the refrigerant recovery tank. The driver could be a fluid pump, a weep hole between the stabilizer concentrate reservoir and recirculating refrigerant, gravity feed, or any means to create a pressure differential such as the circulating refrigerant or a temperature difference. The temperature difference can be attained by employing heat as from an electric heating element or by cooling as from expansion of at least some portion of the refrigerant in the recovery/recycle unit.

Another means to deliver stabilizer(s) to a system already containing a full charge of refrigerant and lubricant is to incorporate the stabilizer(s) into a small in-line vessel. The vessel could be a separate vessel or the stabilizer(s) could be incorporated into a filter/drier design. Filter/driers are already used in air-conditioning and refrigeration systems. The stabilizer(s) could be delivered to the system en total or the vessel could contain a support or media that would provide release of stabilizer(s) over time.

Refrigerant/lubricant stabilizers that are soluble in compressor lubricant can be introduced into the lubricant by various means at different points during manufacture of the refrigerant or later once the refrigerant has been charged to an air-conditioning system. Stabilizer can be added by in-line injection using metering valves and mass flow meters to meter in a pre-determined amount of stabilizer. In such fashion, stabilizer could be added during product blending or product packaging. Alternatively, stabilizer can be pumped into a blending tank containing the lubricant. Load cells would facilitate addition of stabilizer to the proper amount by weight difference. Stabilizer may also be added to lubricant by using density versus temperature data to convert the desired weight of stabilizer to a volume. The required volume of stabilizer could then be pumped or fed by gravity to the lubricant blend tank.

Compatible materials of construction are required for recovery, recycle, and reclamation of refrigerants such as HFOs and azeotropes and blends of HFOs with other desirable refrigerant components. Low GWP refrigerants such as 1234yf/$CF_3I$ have solubility characteristics that differ from CFCs, HCFCs, and HFCs of the past. Metals, plastics, and elastomers that constitute refrigerant wetted parts must be compatible with the refrigerant. $CF_3I$ can react with metals. Passive metals, whether elemental, alloyed, or chemically treated (electrolytic processes, chemical conversion processes, or surface active chemicals) can be used to produce compatible metals for use in refrigerant service equipment such as recovery/recycle machines or reclamation units.

What is claimed is:

1. A composition consisting essentially of about 95 to about 99.9 weight percent HFO-1234yf and about 0.1 to about 5 weight percent farnesene.

2. The composition of claim 1 consisting essentially of about 99 to about 99.7 weight percent HFO-1234yf and about 0.3 to about 1 weight percent farnesene.

3. The composition of claim 1 having a temperature of greater than about 50° C.

4. A method for chemically stabilizing a refrigerant composition comprising HFO-1234yf comprising:

mixing HFO-1234yf with farnesene to form a mixture consisting essentially of about 95 to about 99.9 weight percent HFO-1234yf and about 0.1 to about 5 weight percent farnesene.

5. A method for chemically stabilizing a solvent comprising HFO-1234yf comprising the steps of:

a. mixing HFO-1234yf with farnesene to form a mixture consisting essentially of about 95 to about 99.9 weight percent HFO-1234yf and about 0.1 to about 5 weight percent farnesene; and b. increasing the temperature of the solvent to at least 50° C.

* * * * *